US012551622B2

(12) United States Patent
Bhargava et al.

(10) Patent No.: US 12,551,622 B2
(45) Date of Patent: Feb. 17, 2026

(54) DUAL CHAMBER SYRINGE ASSEMBLY WITH FLOATING STOPPER

(71) Applicant: Becton, Dickinson and Company, Franklin Lakes, NJ (US)

(72) Inventors: Divik Bhargava, Meerut (IN); Shreyasi Dutta, Bangalore (IN); Reddy Jairam Satwik, Visakhapatnam (IN)

(73) Assignee: Becton, Dickinson and Company, Franklin Lakes, NJ (US)

( * ) Notice: Subject to any disclaimer, the term of this patent is extended or adjusted under 35 U.S.C. 154(b) by 652 days.

(21) Appl. No.: 17/983,621

(22) Filed: Nov. 9, 2022

(65) Prior Publication Data

US 2024/0148973 A1 May 9, 2024

(51) Int. Cl.
*A61M 5/19* (2006.01)
*A61M 5/31* (2006.01)
*A61M 5/315* (2006.01)

(52) U.S. Cl.
CPC ............ *A61M 5/19* (2013.01); *A61M 5/3134* (2013.01); *A61M 5/3135* (2013.01); *A61M 5/31513* (2013.01)

(58) Field of Classification Search
CPC ............ A61M 5/19; A61M 2005/1787; A61M 2005/3128; A61M 2039/2426
See application file for complete search history.

(56) References Cited

U.S. PATENT DOCUMENTS 9,636,469 B2 5/2017 Zivkovic et al.
2006/0142701 A1* 6/2006 Thorne, Jr. ....... A61M 5/31596 604/218
2014/0228746 A1 8/2014 Li et al.
2022/0134003 A1 5/2022 Rivier et al.

OTHER PUBLICATIONS

"PCT International Search Report and Written Opinion in PCT/US2023/036232 dated Mar. 4, 2024, 15 pages".

* cited by examiner

*Primary Examiner* — Bradley J Osinski
(74) *Attorney, Agent, or Firm* — Servilla Whitney LLC

(57) ABSTRACT

A dual chamber syringe facilitates selective drug mixing, dosing, and administration, as well as pre- or post-administration flushing with a single syringe instrument. A syringe barrel incorporates an outlet, as well as variable-volume, primary and secondary fluid chambers, separated by a floating stopper. The floating stopper defines a dome-shaped split septum with a central slit at its apex. The split septum is a bi-stable valve, closing the central slit by compression in its meridial dimension when the septum is in a first, relaxed state, and opening the central slit when the septum is buckled or flipped under tension in the meridial dimension in a second state. Buckling of the septum wall is caused solely by differential fluid pressure applied by a single plunger, without physical contact of the septum with any other structure within the syringe.

27 Claims, 4 Drawing Sheets

DUAL CHAMBER SYRINGE ASSEMBLY WITH FLOATING STOPPER

TECHNICAL FIELD

The present disclosure generally relates to a dual chamber syringe assembly for administering two gases or fluids, or for administering and flushing catheters and other vascular accessing devices (VADs), or for mixing and administering fluids, and methods of flushing a catheter.

BACKGROUND

VADs are commonly used therapeutic devices and include I.V. catheters. There are two general classifications of VADs: peripheral catheters and central venous catheters. If not properly maintained, VADs can become occluded. To ensure VADs are used properly and do not become occluded, standards of practice have been developed. These standards include a cleaning procedure, which is commonly referred to as a flush procedure or flushing a catheter.

VAD standards of practice usually recommend flush procedures be performed after catheter placement, before fluid infusion, and before and after drug administration, blood sampling, transfusions, and parenteral nutrition. The goal of these flush procedures is to confirm catheter patency, avoid drug incompatibilities, ensure the complete drug dose administration, prevent thrombus formation, and minimize the risk of blood stream infections. Flush procedures require several types and amounts of flush solutions. Commonly used flush solutions are saline and/or heparin lock solution. The type of flush solution and amount vary depending on the specific type of catheter. Flush solution volumes between 5 and 10 ml are most common but can range from 1 ml to 20 ml.

For flush procedures, an I.V. line refers to a system containing a VAD, a tubing set with clamp and may terminate with a port or valve. The most common types of ports are covered by pierceable septums or pre-slit septums and are known in the art and sometimes referred to as “PRN” from the Latin pro re nata meaning “as the need arises”. The septum is preferably made of rubber or another elastomeric material, which permits insertion of a sharp needle cannula to infuse fluids or to withdraw fluids from the catheter. Upon withdrawal of the needle cannula the septum seals itself. Ports having pre-slit septums are used with blunt cannula or the frusto-conically shaped tip of a syringe barrel. The syringe tip or the blunt cannula (which is usually attached to a syringe) is gently pushed through the pre-slit septum to establish fluid communication.

I.V. valves, another type of terminal I.V. access device that does not require a needle having a sharp tip, are activated by the frusto-conically shaped tip of a syringe barrel to allow fluid communication between the interior of the syringe and the catheter. These valves may contain structure for delivering fluid from a storage compartment in the valve to the catheter and are referred to in the art as positive displacement valves.

The removal of debris or residue is referred to as “purging” or “flushing” and prevents the build-up of deposits of blood, blood residue and I.V. drugs within a catheter or other VAD device. Such build-up can cause partial or complete blockage of the fluid pathway in a catheter system and can also require expensive and potentially dangerous methods for purging the affected catheter or a total catheter exchange. Often, such blockages lead to interruptions in therapy that may compromise patient care. The build-up of residue within a catheter can also increase infection risk by providing a breeding medium for microorganisms.

As is understood by one skilled in the art, flushing techniques involve injecting a flush solution, e.g., a saline solution, into VADs to clear debris and blockage. Injection is commonly done by a advancing a plunger rod into a pre-filled syringe barrel thereby expelling the flush solution into the VAD. When such techniques are used in conjunction with catheters, turbulence is introduced within the catheter, moving any debris or residue attached to the catheter. Flushing techniques require the application of substantially constant pressure or force to the plunger rod in the distal direction. Conventional or smooth flushing techniques may also include the application of pressure or force that increases or decreases substantially linearly to the plunger rod in the distal direction.

After flushing, the practitioner is then able to administer a dosage of medical fluid, the fluid being in a vial which requires withdrawal therefrom, or in a separate pre-filled syringe. However, the connecting of multiple devices to a VAD introduces the connectors to an unsterile outside environment, thereby introducing the possibility of transmitting a catheter related bloodstream infection (CRBSI), which can be costly and potentially lethal. To decrease CRBSI cases and to ensure VAD's are used and maintained correctly, standards of practice have been developed, which include disinfecting and cleaning procedures.

Administration of intravenous medication followed by I.V. flush, typically utilize two separate syringes in clinical practice.

There is a need for a syringe assembly which has the means to both flush a VAD and administer a dosage of medical fluid, thereby reducing the risk of CRBSI. There is also a need for a single syringe for administration of intravenous medication followed by I.V. flush, to increase clinician efficiency, and reduce costs associated with maintaining syringe inventory, and medical waste disposal.

SUMMARY

A dual chamber syringe facilitates selective drug mixing, dosing, and administration through catheters or other vascular accessing devices (VADs), as well as pre- or post-administration flushing of catheters with a single syringe instrument. A barrel of the syringe incorporates an outlet, as well as variable-volume, primary and secondary fluid chambers, separated by a floating stopper. A plunger is capable of selective translation within the barrel interior. The floating stopper defines a dome-shaped split septum with a central slit at its apex. The split septum is a bi-stable valve, closing the central slit by compression in its meridial dimension when the septum is in a first, relaxed state, and opening the central slit when the septum is buckled under tension (i.e., flipped) in the meridial dimension in a second state. Buckling or flipping of the septum wall is caused solely by differential fluid pressure applied by the plunger without physical contact of the septum with any other structure within the syringe. The isolated, secondary chamber construction advantageously facilitates use of pre-packaged drugs or flushing solutions in that chamber. Use of syringes of the type disclosed herein, in medical procedures requiring both flushing and administration of drugs through catheters or other VADs, reduces the need to perform multiple infusions and withdrawals of multiple, single-function syringes. Use of the disclosed syringes advantageously reduces risk of patient infection, reduces costs associated with syringe inventory and subsequent waste disposal, and reduces clinician time necessary to complete the associated medical procedures.

One aspect of the present disclosure pertains to a syringe comprising a substantially cylindrically shaped barrel, which defines a first inner side wall. The barrel has an open proximal end, and a distal end, with the distal end of the barrel including a connector defining an outlet lumen therethrough. The outlet lumen is in fluid communication with an interior of the barrel; the interior is defined by the open proximal end, the distal end, and the first inner side wall of the barrel. The syringe includes a plunger having proximal and distal ends, with the distal end thereof disposed within the barrel interior. The plunger is capable of selective translation within the barrel interior along an axis thereof. A plunger stopper is coupled to the distal end of the plunger, with the plunger stopper having a distal end surface facing the distal end of the barrel. A monolithic, unistructural, floating stopper is oriented in the barrel interior and translatable between the plunger stopper and the distal end of the barrel. The floating stopper has a drum-shaped side wall defining a stopper internal cavity in open communication with a first axial end thereof. A second axial end of the drum-shaped side wall is cojoined with a circumferential base of a dome-shaped septum defining an apex. A wall forming the septum has a first face in communication with the stopper internal cavity, and a second face. The septum wall further defines a central slit piercing both its first and second faces at the apex. The septum wall of the dome-shaped septum forms a bi-stable valve, closing the central slit by compression in its meridial dimension when the septum is in a first, relaxed state, and opening the central slit when the septum is buckled under tension in the meridial dimension in a second state. The opened central slit allows pressurized fluid to flow from the internal stopper cavity out of the second face of the septum, with buckling of the septum wall caused solely by higher differential fluid pressure in the stopper internal cavity on the first face than on its second face, without physical contact of the septum wall with any other structure within the syringe. A primary fluid chamber, within the barrel interior, is defined between the septum of the floating stopper and the outlet lumen. The primary fluid chamber is in fluid communication with the central slit of the septum; volume of the primary fluid chamber is selectively variable by translation of the plunger. The syringe has a secondary fluid chamber within the barrel interior, defined between the distal end surface of the plunger stopper and the septum of the floating stopper. The secondary fluid chamber is in fluid communication with the central slit of the septum; volume and fluid pressure within the secondary fluid chamber is selectively variable by translation of the plunger. When the central slit of the septum is closed, the secondary fluid chamber is isolated from the outlet lumen, so that translation of the plunger only aspirates fluid into or dispenses fluid out of the primary chamber, via the outlet lumen. When the central slit of the septum is opened by increasing differential fluid pressure in the secondary fluid chamber and in the stopper internal cavity, sufficient to buckle the wall of the dome-shaped septum into its second state, the secondary fluid chamber is in fluid communication with the outlet lumen, so that further translation of the plunger toward the distal end of the barrel dispenses fluid out of the secondary chamber, via the outlet lumen.

In some embodiments of the syringe disclosed herein, its secondary chamber is pre-filled with flushing solution. Desirably, in those embodiments, a clinician can administer a medication into a patient's VAD with the primary chamber and immediately flush the VAD with the second chamber, without removing the syringe from the VAD, with a single, continuous advancement of the plunger, and without manipulation of additional valves or plungers.

Another aspect of the present disclosure pertains to a syringe comprising a substantially cylindrically shaped barrel, which defines a first inner side wall, with the barrel having an open proximal end, and a distal end. The distal end of the barrel includes a connector defining an outlet lumen therethrough, with the outlet lumen in fluid communication with an interior of the barrel. The barrel interior is defined by the open proximal end, the distal end, and the first inner side wall of the barrel. The syringe includes a plunger having proximal and distal ends; the distal end thereof is disposed within the barrel interior. The plunger is capable of selective translation within the barrel interior along an axis thereof. A plunger stopper is coupled to the distal end of the plunger. The plunger stopper has a distal end surface facing the distal end of the barrel. A monolithic, unistructural, floating stopper is oriented in the barrel interior and is translatable between the plunger stopper and the distal end of the barrel. The floating stopper has a drum-shaped side wall defining a stopper internal cavity in open communication with a first axial end thereof. A second axial end of the drum-shaped side wall is cojoined, by an intermediary, annular-shaped, flexible hinge, with a circumferential base of a dome-shaped septum defining an apex. A wall forming the septum has a first face in communication with the stopper internal cavity, and a second face. The septum wall defines a central slit piercing both its first and second faces at the apex. The septum wall of the dome-shaped septum forms a bi-stable valve, closing the central slit by compression in its meridial dimension when the septum is in a first, relaxed state, with the apex is closer to the first axial end of the drum-shaped side wall, and opening the central slit when the septum is buckled under tension in the meridial dimension in a second state, with the apex further away from the first axial end of the drum-shaped side wall. The opened central slit allows pressurized fluid to flow from the internal stopper cavity out of the second face of the septum, with buckling of the septum wall caused solely by higher differential fluid pressure in the stopper internal cavity on the first face than on its second face, without physical contact of the septum wall with any other structure within the syringe. A primary fluid chamber within the barrel interior is defined between the septum of the floating stopper and the outlet lumen. The primary fluid chamber is in fluid communication with the central slit of the septum; volume of the primary fluid chamber is selectively variable by translation of the plunger. A secondary fluid chamber within the barrel interior is defined between the distal end surface of the plunger stopper and the septum of the floating stopper; the secondary fluid chamber is in fluid communication with the central slit of the septum. Volume and fluid pressure within the secondary fluid chamber is selectively variable by translation of the plunger. When the central slit of the septum is closed the secondary fluid chamber is isolated from the outlet lumen, so that translation of the plunger only aspirates fluid into or dispenses fluid out of the primary chamber, via the outlet lumen. When the central slit of the septum is opened by increasing differential fluid pressure in the secondary fluid chamber and in the stopper internal cavity, sufficient to buckle the wall of the dome-shaped septum into its second state, the secondary fluid chamber is in fluid communication with the outlet lumen, so that further translation of the plunger toward the distal end of the barrel dispenses fluid out of the secondary chamber, via the outlet lumen.

Another aspect of the present disclosure pertains to a syringe comprising a substantially cylindrically shaped barrel, which defines a first inner side wall. The barrel has an open proximal end, and a distal end, with the distal end of the barrel including a connector defining an outlet lumen therethrough. The outlet lumen is in fluid communication with an interior of the barrel, with the interior defined by the open proximal end, the distal end, and the first inner side wall of the barrel. The syringe includes a plunger having proximal and distal ends, with the distal end thereof disposed within the barrel interior. The plunger is capable of selective translation within the barrel interior along a barrel axis thereof. A plunger stopper is coupled to the distal end of the plunger, the plunger stopper has a distal end surface facing the distal end of the barrel. A monolithic, unistructural, floating stopper is oriented in the barrel interior and translatable between the plunger stopper and the distal end of the barrel. The floating stopper has a drum-shaped side wall defining a stopper internal cavity in open communication with a first axial end thereof. A second axial end of the drum-shaped side wall is cojoined with a circumferential base of a dome-shaped septum defining an apex. A wall forming the septum has a first face in communication with the stopper internal cavity, and a second face in opposed orientation with the distal end of the barrel. The septum wall defines a central slit piercing both its first and second faces at the apex. The floating stopper further defines a skirt having a first axial face concentrically joined to the second face of the septum wall by an annular skirt hinge that circumscribes the central slit, and a second axial face, projecting from the skirt hinge, in opposed orientation with the distal end of the barrel. The septum wall of the dome-shaped septum forms a bi-stable valve, closing the central slit by compression in its meridial dimension when the septum is in a first, relaxed state, with the apex closer to the first axial end of the drum-shaped side wall, and opening the central slit when the septum is buckled under tension in the meridial dimension in a second state, with the apex farther away from the first axial end of the drum-shaped side wall. The opened central slit allows pressurized fluid to flow from the internal stopper cavity out of the second face of the septum, with buckling of the septum wall caused solely by higher differential fluid pressure in the stopper internal cavity on the first face than on its second face, without physical contact of the septum wall with any other structure within the syringe. A primary fluid chamber, within the barrel interior, is defined between the septum of the floating stopper and the outlet lumen. The primary fluid chamber is in fluid communication with the central slit of the septum; volume of the primary fluid chamber is selectively variable by translation of the plunger. A secondary fluid chamber within the barrel interior, is defined between the distal end surface of the plunger stopper and the septum of the floating stopper. The secondary fluid chamber is in fluid communication with the central slit of the septum; volume and fluid pressure within the secondary fluid chamber is selectively variable by translation of the plunger. When the central slit of the septum is closed the secondary fluid chamber is isolated from the outlet lumen, so that translation of the plunger only aspirates fluid into or dispenses fluid out of the primary chamber, via the outlet lumen. When the central slit of the septum is opened by increasing differential fluid pressure in the secondary fluid chamber and in the stopper internal cavity, sufficient to buckle the wall of the dome-shaped septum into its second state, the skirt folds or pivots about the annular skirt hinge toward the second face of the septum wall, and the secondary fluid chamber is in fluid communication with the outlet lumen. Further translation of the plunger toward the distal end of the barrel dispenses fluid out of the secondary chamber, via the outlet lumen.

The respective features of the aspects and exemplary embodiments of the disclosure that are described herein may be applied jointly or severally in any combination or sub-combination.

BRIEF DESCRIPTION OF THE DRAWINGS

Exemplary embodiments of the disclosure are further described in the following detailed description in conjunction with the accompanying drawings, in which.

To facilitate understanding, identical reference numerals have been used, where possible, to designate identical elements that are common to the figures. The figures are not drawn to scale.

DETAILED DESCRIPTION

Figure 1:
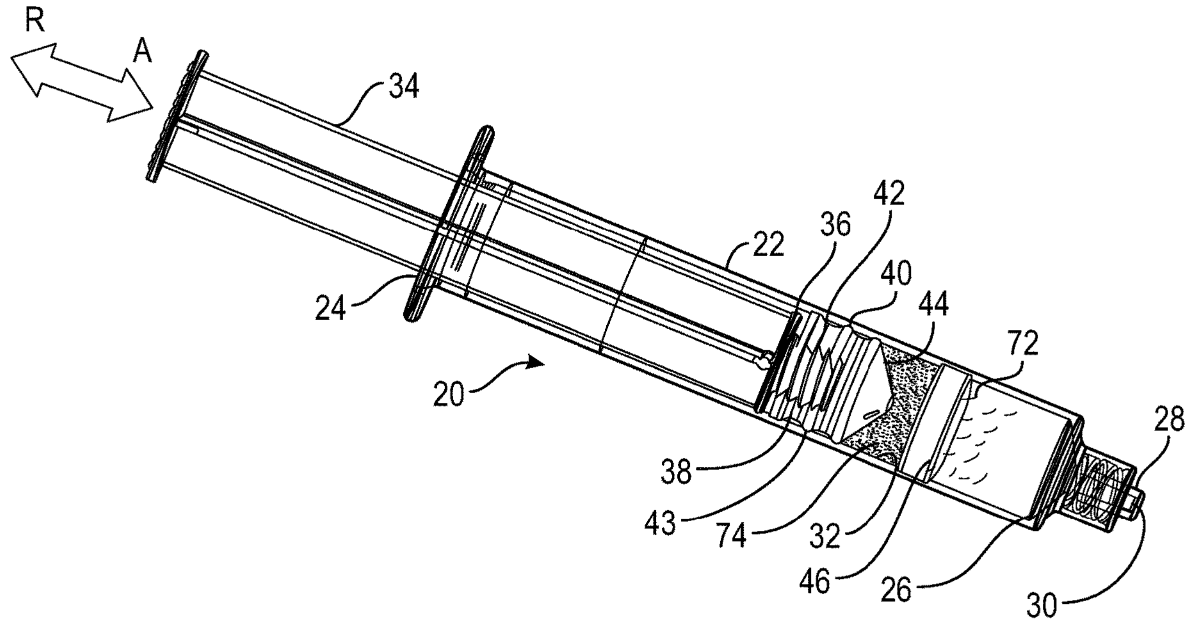
FIG. 1 is a cross-sectional view of an embodiment of a dual chamber syringe, where each of the primary and secondary chambers contain fluid, isolated from each other by the floating stopper.

Aspects of the dual chamber syringe embodiments disclosed herein facilitate selective drug mixing, dosing, and administration through catheters or other vascular accessing devices (VADs), as well as pre- or post-administration flushing of catheters with a single syringe instrument. Generally, in each disclosed embodiment, the syringe comprises a substantially cylindrically shaped barrel, which defines a first inner side wall. The barrel has an open proximal end, and a distal end; the distal end of the barrel includes a connector defining an outlet lumen therethrough, such as a Luer connector. The outlet lumen is in fluid communication with an interior of the barrel. The barrel interior is defined by its open proximal end, the distal end, and the first inner side wall. A plunger has a distal end with a plunger stopper disposed within the barrel interior; the plunger is capable of selective translation within the barrel interior. A monolithic, unistructural, floating stopper is oriented in the barrel interior and translatable between the plunger stopper and the distal end of the barrel. The floating stopper has a drum-shaped side wall defining a stopper internal cavity in open communication with its first axial end. A second axial end of the drum-shaped side wall is cojoined with a circumferential base of a dome-shaped septum defining an apex. A wall forming the septum has a first face in communication with the stopper internal cavity, and a second face. The septum wall further defines a central slit piercing both its first and second faces at the apex. The septum wall forms a bi-stable valve, closing the central slit by compression in its meridial dimension when the septum is in a first, relaxed state, and opening the central slit when the septum is buckled under tension in the meridial dimension (i.e., flipped) in a second state. When the central slit is opened, it allows pressurized fluid to flow from the internal stopper cavity out of the second face of the septum. Buckling of the septum wall is caused solely by higher differential fluid pressure in the stopper internal cavity on the first face than on its second face, without physical contact of the septum wall with any other structure within the syringe. The differential pressure is generated by translating the plunger towards the distal end of the barrel.

The floating stopper separates the barrel interior into a primary fluid chamber, defined between itself and the distal end of the barrel; and a secondary fluid chamber defined between itself and the plunger stopper. When the central slit of the septum is closed the secondary fluid chamber is isolated from the outlet lumen, so that translation of the plunger only aspirates fluid into or dispenses fluid out of the primary chamber, via the outlet lumen. When the central slit of the septum is opened by increasing differential fluid pressure in the secondary fluid chamber and in the stopper internal cavity, sufficient to buckle or flip the wall of the dome-shaped septum into its second state, the secondary fluid chamber is in fluid communication with the outlet lumen, so that further translation of the plunger toward the distal end of the barrel dispenses fluid out of the secondary chamber, via the outlet lumen.

The isolated, secondary chamber construction advantageously facilitates use of pre-packaged drugs or flushing solutions in that chamber, whereby a clinician can aspirate and dispense medication with the empty primary chamber and thereafter immediately deliver pre-packaged flushing solution from the secondary chamber, in a single plunger stroke, without manipulation of additional plungers, manual valves or locks. In other embodiments, the syringe disclosed herein is used as a drug mixing syringe, prepackaged with a powdered drug in the primary chamber and a diluent solution in the secondary chamber. In some embodiments, a single advancing stroke on the single plunger of the syringe automatically delivers or infuses, sequentially into the VAD, a drug contained in the primary chamber, followed by flushing solution.

In this disclosure, a convention is followed wherein the distal end of the device is the end closest to a patient, e.g., for delivery of one or more drugs to the patient, and the proximal end of the device is the end away from the patient and closest to a clinician or other medical practitioner. With respect to terms used in this disclosure, the following definitions are provided.

As used herein, the use of "a," "an," and "the" includes the singular and plural.

As used herein, the term "Luer connector" refers to a connection collar that is the standard way of attaching syringes, catheters, hubbed needles, I.V. tubes, etc. to each other. The Luer connector consists of male and female interlocking tubes, slightly tapered to hold together better with even just a simple pressure/twist fit. Luer connectors can optionally include an additional outer rim of threading, allowing them to be more secure. The Luer connector male end is associated with a flush syringe and can interlock and connect to the female end located on the vascular access device (VAD). A Luer connector also has a distal end channel that releasably attaches the Luer connector to the hub of a VAD, and a proximal end channel that releasably attaches the Luer connector to the barrel of a syringe.

As used herein, ISO 80369-7:2016 defines a specification for standard Luer connectors including a 6% taper between the distal end and the proximal end. A male standard Luer connector increases from the open distal end to the proximal end. A female standard Luer connector decreases from the open proximal end to the distal end. According to ISO 80369-7:2016, a male standard Luer connector has an outer cross-sectional diameter measured 0.75 mm from the distal end of the tip of between 3.970 mm and 4.072 mm. The length of the male standard Luer taper is between 7.500 mm to 10.500 mm. The outer cross-sectional diameter measured 7.500 mm from the distal end of the tip is between 4.376 mm and 4.476 mm. As used herein, the phrases "male standard Luer connector" and "female standard Luer connector" shall refer to connectors having the dimensions described in ISO 80369-7, which is hereby incorporated by reference in its entirety.

As would be readily appreciated by skilled artisans in the relevant art, while descriptive terms such as "tip", "hub", "thread", "protrusion/insert", "tab", "slope", "wall", "top", "side", "bottom" and others are used throughout this specification to facilitate understanding, it is not intended to limit any components that can be used in combinations or individually or to require specific spatial orientations, to implement various aspects of the embodiments of the present disclosure.

Before describing several exemplary embodiments of the disclosure, it is to be understood that the disclosure is not limited to the details of construction or process steps set forth in the following description. The disclosure is capable of other embodiments and of being practiced or being conducted in many ways.

The matters exemplified in this description are provided to assist in a comprehensive understanding of exemplary embodiments of the disclosure. Accordingly, those of ordinary skill in the art will recognize that various changes and modifications of the embodiments described herein can be made without departing from the scope and spirit of the disclosure. Also, descriptions of well-known functions and constructions are omitted for clarity and conciseness.

In an exemplary implementation of the embodiments of present disclosure, a barrel of a syringe includes a distal end having a needleless connection. In one or more embodiments, the needleless connection includes at least one thread and other features in all combinations allowing it to interface with a corresponding thread or plurality of threads of a corresponding connector.

According to further exemplary implementations of the embodiments of the present disclosure, configuration of structural elements making up the needleless connector include a collar protruding from the distal end of the barrel, the collar comprising at least one thread to connect to the corresponding thread or plurality of threads of a corresponding connector. According to further exemplary implementations of the embodiments of the present disclosure, the syringe incorporates a needle-type connector for drug aspiration from a vial, rather than a needleless connector.

According to still further exemplary implementations of the embodiments of the present disclosure, the collar or the needleless connector may bend or elastically deform to allow better interference fit compliance with corresponding connectors.

According to still further exemplary implementations of the embodiments of the present disclosure, the needleless connector may comprise female threads that are sized and have a thread pattern that will engage with a standard ISO594-2 type of male fitting and/or male threads that are sized and have a thread pattern that will engage with a standard ISO594-2 type of female fitting. An example of an ISO594-2 type of fitting is a Q-style fitting. According to still further exemplary implementations of the embodiments of the present disclosure, the needleless connector may be used with needle type connectors for drug aspiration from a vial.

In one or more embodiments, a female connector may be selected from the group consisting essentially of: needle-type connectors (for direct injection into a patient or insertion into a drug vial for aspiration of a drug dose therefrom), needle-free connectors, catheter Luer connectors, stopcocks, and hemodialysis connectors. In one or more embodiments, the needleless connector is selected from a Q-Syte connector, MaxPlus, MaxPlus Clear, MaxZero, UltraSite, Caresite, InVision-Plus, Safeline, OneLink, V-Link, ClearLink, NeutraClear, Clave, MicroClave, MicroClave Clear, Neutron, NanoClave, Kendall, Nexus, InVision, Vadsite, Bionector, etc. In one or more embodiments, the male connector may be an intravenous tubing end or a stopcock.

Figure 2:
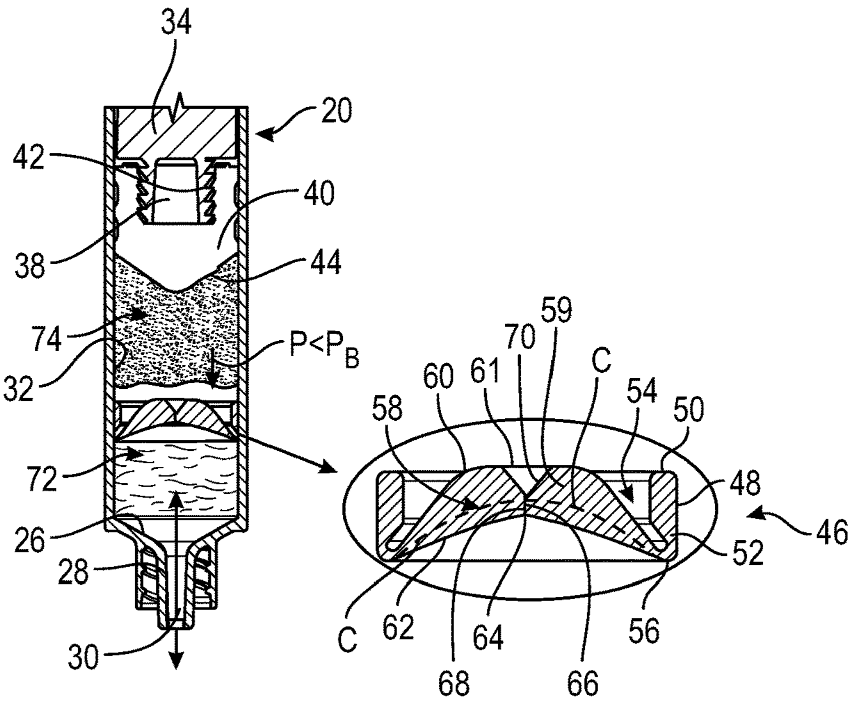
FIG. 2 is a detailed cross-sectional view of the syringe of FIG. 1 shown dispensing fluid from the primary chamber with the floating stopper isolating fluid in the secondary chamber.
Figure 3:
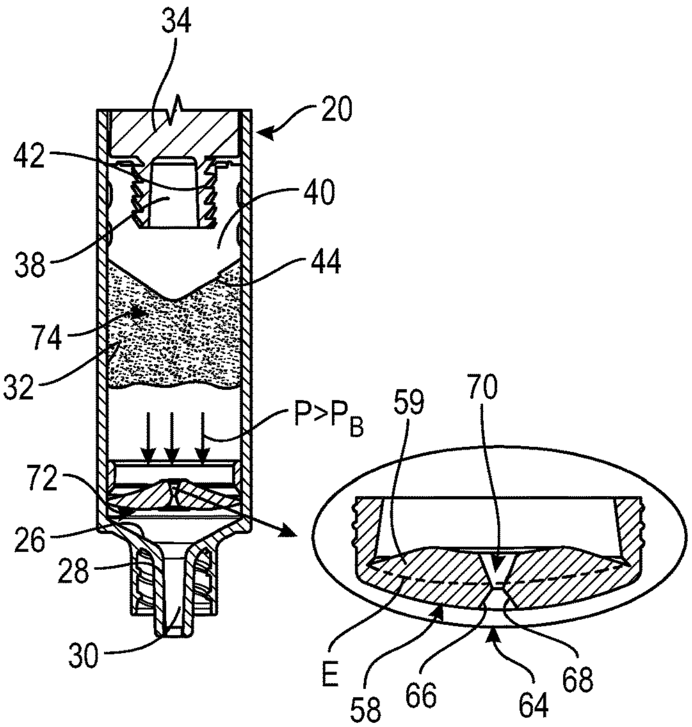
FIG. 3 is a detailed cross-sectional view of the syringe of FIG. 1, dispensing fluid from secondary chamber through the floating stopper.

Referring now to the drawings, a first aspect of the present disclosure is shown in FIGS. 1-3. wherein a syringe 20 comprises a substantially cylindrically shaped barrel 22, which defines an open proximal end 24, and a distal end 26. The distal end 26 of the barrel 22 includes a Luer connector 28 defining an outlet lumen 30, for attachment to and fluid communication with various associated VAD connectors (not shown). An interior of the barrel 22 is generally defined and bounded by its inner side wall 32, open proximal end 24, and its distal end 26. The outlet lumen 30 is in fluid communication with the interior of the barrel. A plunger 34 is capable of selective translation within the barrel interior. The plunger 34 has a distal end 36 with male threads 38 for coupling to a plunger stopper 40 by mating female threads 42 formed in the stopper. The mating male 38 and female 42 threads collectively comprise a connection feature to removably or non-removably couple the plunger 34 and plunger stopper 40. Alternatively, in one or more embodiments, the connection feature couples the plunger 34 and the plunger stopper 40 by way of an interference fit. In one or more embodiments, the connection feature couples the plunger 34 and the plunger stopper 40 by way of a snap fit. In one or more embodiments, the connection feature couples the plunger 34 and the plunger stopper 40 by way of a twist-lock fit. In one or more embodiments, the connection feature couples the plunger 34 and the plunger stopper 40 by way of sonic welding or a medical grade adhesive. In one or more embodiments, plunger stopper 40 is integrally formed to the distal end 36 of the plunger 34. The plunger stopper 40 incorporates radially oriented ribs 43 and a distal end 44 that faces the distal end 26 of the syringe barrel 22. The distal end 44 of the plunger stopper 40 has an outwardly conical shape. In one or more embodiments, the distal end 44 has a frustoconical shape.

A monolithic, unistructural, floating stopper 46 is oriented in the barrel interior and is translatable between the plunger stopper 40 and the distal end 26 of the syringe barrel 22. The floating stopper 46 has a drum-shaped side wall 48, with a first axial end 50 facing the plunger stopper 40, a second axial end 52 facing the distal end 26 of the syringe barrel 22, and an internal cavity 54 that is in open communication with its first axial end 50. The second axial end 52 of the drum-shaped side wall 48 is cojoined, by an intermediary, annular-shaped, flexible hinge 56, with a circumferential base of a dome-shaped septum 58. A wall 59 forming the septum 58 has a first face 60, forming an apex 61 of the dome, and is in communication with the internal cavity 54. The wall 59 forming the septum has a second face 62 opposite its first face 60. In the embodiment of FIGS. 1-3, wall thickness of the dome-shaped septum 58 increases from its base at the hinge 56 to its apex 61. In other embodiments, wall thickness of the dome-shaped septum is uniform. The dome-shaped septum 58 defines a central slit 64 between meridianally-oriented, third 66 and fourth 68 separable faces of its wall 59. The central slit 64 pierces both its first 60 and second faces 62 at the apex 61. The first face 60 of the septum wall 59 defines a notch 70 outwardly diverging from the central slit 64 towards the first axial end 50 of the floating stopper 46. In some embodiments, the floating stopper 46 comprises a molded, elastomer material, such as isoprene rubber.

The floating stopper 46 separates the interior of the syringe barrel 22 into a primary fluid chamber 72, defined between itself and the distal end 26 of the barrel; and a secondary fluid chamber 74 defined between itself and the plunger stopper 40. Translation of the plunger 34 generates a differential pressure P on the floating stopper 46, wherein withdrawing the plunger translates the floating stopper towards the proximal end 24 of the syringe barrel 22. Conversely, advancing the plunger 34 translates the floating stopper 46 towards the distal end 26 of the syringe barrel 22. When the central slit 64 of the dome-shaped septum 58 is closed, the secondary fluid chamber 74 is isolated from the outlet lumen 30, so that translation of the plunger 34 only aspirates fluid into or dispenses fluid out of the primary chamber 72, via the outlet lumen 30.

The septum wall 59 of the dome-shaped septum 58 forms a bi-stable valve; the valve closes the central slit 64 by compression in its meridial dimension (dotted line C of FIG. 2) when the septum is in a first, default, relaxed state, with its the apex 61 closer to the first axial end 50 of the drum-shaped side wall 48. The dome-shaped septum 58 remains in its relaxed, closed, state unless and until it is buckled and extended under tension, in its meridial dimension (i.e., flipped, as shown by the dashed line E of FIG. 3) in a second state, with its apex 61 further away from the first axial end 50 of the drum-shaped side wall 48. When the dome-shaped septum 58 is in its second, buckled state, its central slit 64 opens, allowing fluid to flow out of the secondary chamber 74, through the internal stopper cavity 54, out of its second face 62. Thereafter the fluid flows through the primary chamber 72, whereupon it is dispensed or discharged through the outlet lumen 30.

Buckling or flipping of the wall 59 of the dome-shaped septum 58 is caused solely by application of sufficiently high, buckling differential fluid pressure $P_B$, on the floating stopper 46 by pressing and translating the plunger 34 towards the distal end 26 of the barrel 22. When the plunger 34 is pressed with sufficient force to exceed the buckling differential fluid pressure level $P_B$ within the internal cavity 54 of the floating stopper 46 on the first face 60 of the dome-shaped septum 58, its septum wall 59 buckles to its second state shown in FIG. 3, without physical contact of the septum wall with any other structure within the syringe 20. When differential pressure P on the first face 60 falls below the buckling differential pressure $P_B$, the dome-shape stopper 58 relaxes to its first state, closing the central slit 64, thereby re-closing the bi-stable valve and re-isolating the secondary chamber 74 from the first chamber 72. In some embodiments, the buckling differential pressure $P_B$ is greater than approximately 30 pounds per square inch (2.07 bar).

In one or more embodiments of the syringe 20, the primary chamber 72 is pre-filled or filled on site with a desired medicine. In one or more embodiments, the secondary chamber 74 is pre-filled with a desired amount of a saline flush fluid. In one or more embodiments, the secondary chamber 74 is filled with a desired medicine. In one or more embodiments, both the primary 72 and secondary 74 chambers are filled with a desired medicine. In one or more embodiments, both the primary 72 and secondary 74 chambers are filled with desired amounts of saline flush fluid. In one or more embodiments, the primary chamber 72 and/or the secondary chamber 74 are pre-filled with fluid during or after the assembly of the syringe 20 using sterile filling methods. In some embodiments, the connector 28 and its outlet lumen 30 are capped (not shown) to prevent fluid leakage from the syringe 20. In some applications, the syringe 20 with a capped connector 28 is utilized to reconstitute a powdered medicine that has been prefilled in the primary chamber 72, by dispersing pre-filled diluent liquid stored in the secondary chamber 74 into the primary chamber prior to uncapping the connector. In other applications, a drug is aspirated and dispensed into a VAD with the primary chamber 72 and subsequently the VAD is flushed with a flushing solution stored in the secondary chamber 74.

Another aspect of the present disclosure is shown in FIGS. 4-10, wherein syringe 80 comprises a substantially cylindrically shaped barrel 82, which defines an open proximal end 84, and a distal end 86. The distal end 86 of the barrel 82 includes a threaded Luer connector 88 defining an outlet lumen 90, for attachment to and fluid communication with various associated VAD connectors (not shown). An interior of the barrel 82 is generally defined and bounded by its inner side wall 92, open proximal end 84, and its distal end 86. The outlet lumen 90 is in fluid communication with the interior of the barrel. A plunger 94 is capable of selective translation within the barrel interior. The plunger 94 has a distal end 95 coupled to plunger stopper 96, by a connector feature of the type previously described with respect to the embodiments of the syringe 20. The plunger stopper 90 incorporates radially oriented ribs 97 and a distal end 98 that faces the distal end 86 of the syringe barrel 82. The distal end 98 of the plunger stopper 96 has an outwardly conical shape. In one or more embodiments, the distal end 98 has a frustoconical shape.

Figure 4:
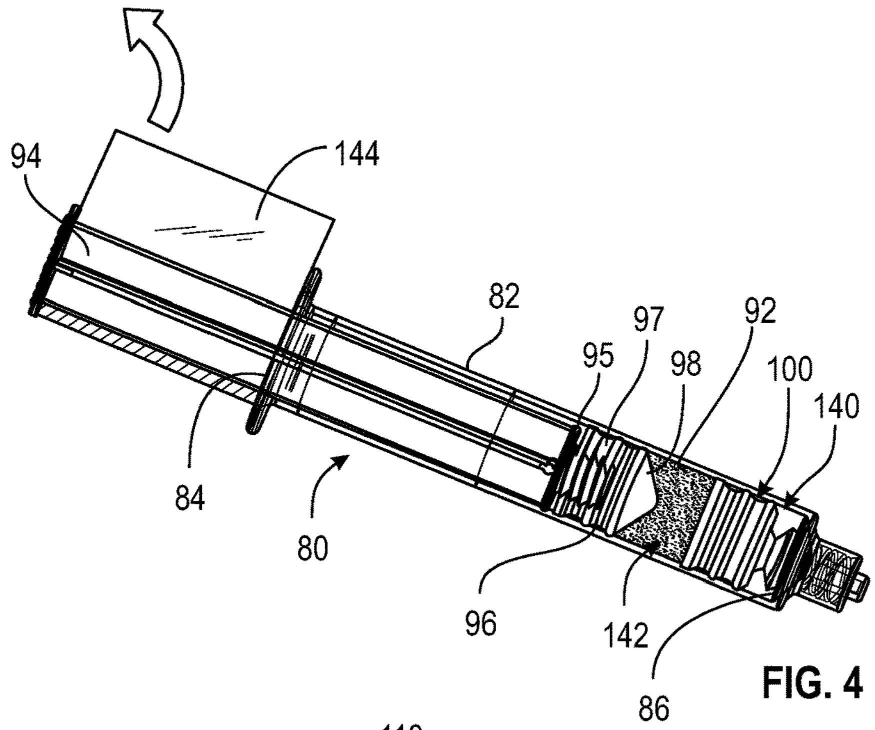
FIG. 4 is a cross-sectional view of another embodiment of a dual chamber syringe, where its secondary chamber contains fluid.
Figure 5:
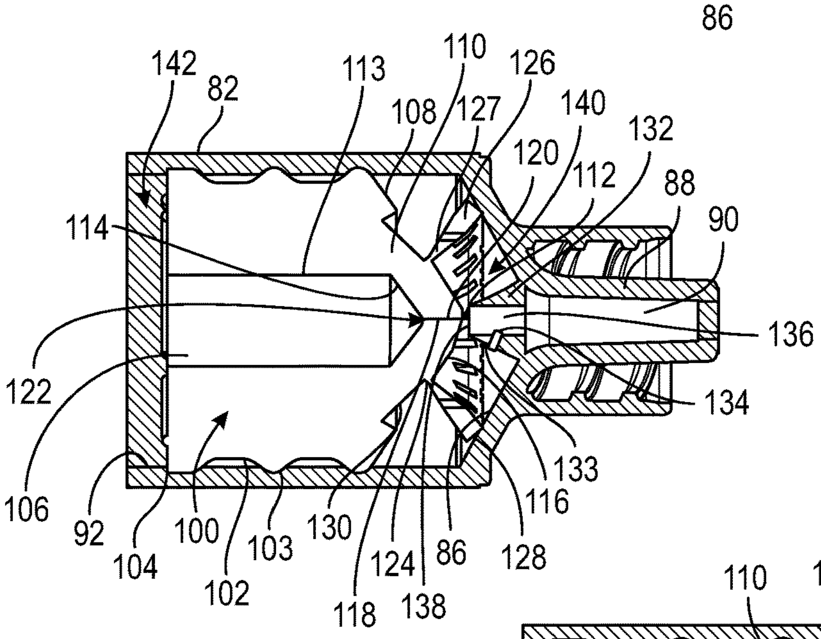
FIG. 5 is an enlarged, partial cross-sectional view of the syringe of FIG. 4.
Figure 6:
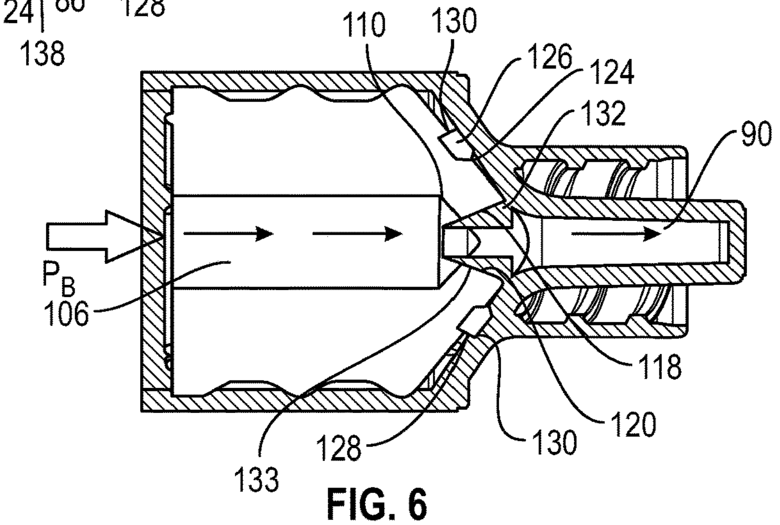
FIG. 6 is an enlarged, partial cross-sectional view of the syringe of FIG. 4, after dispensing fluid from the secondary chamber.

A monolithic, unistructural, floating stopper 100 is oriented in the barrel interior and is translatable between the plunger stopper 96 and the distal end 86 of the syringe barrel 82. The floating stopper 100 has a drum-shaped side wall 102, with radial ribs 103, a first axial end 104 facing the plunger stopper 96, an internal cavity 106 that is in open communication with its first axial end, and a second axial end 108 facing the distal end 86 of the syringe barrel 82. The second axial end 108 of the drum-shaped side wall 102 is cojoined with a circumferential base of a dome-shaped septum 110, which defines an apex 112. A wall 113 forming the septum 110 has a first face 114 in communication with the internal cavity 106 and a second face 116 opposite its first face 114, which defines the apex 112. The second face 116 is in opposed orientation with the distal end 86 of the syringe barrel 82. In the embodiment of FIGS. 4-6, wall 113 thickness of the dome-shaped septum 110 increases from its base at the second axial end 108 of the floating stopper 100 to the apex 112. In other embodiments, wall 113 thickness of the dome-shaped septum is uniform. The dome-shaped septum 110 has meridianally oriented, third 118 and fourth 120 separable faces of its wall 113, which define a central slit 122 there between. The central slit 122 is meridianally oriented, and pierces both of the first 60 and second faces 62 of the dome-shaped septum 110 at the apex 112.

The floating stopper 110 further comprises a generally annular, flexible, skirt hinge 124 coupled to the second face 116 of the dome-shaped septum 110, circumscribing the central slit 122. A frusto-conical-shaped skirt 126 has a smaller diameter, first axial face 127 coupled to the skirt hinge 124 and a larger diameter second axial face 128 that projects away from the skirt hinge, in opposed orientation with the distal end 86 of the syringe barrel 82. Referring to FIG. 6, the skirt 126 is pivotable about the skirt hinge 124, and so that it is capable of folding toward the second face 116 of the dome-shaped septum 110, into a recess 130 that circumscribes the skirt hinge. In other embodiments, the skirt comprises profiles other than a frusto-conical profile. In other embodiments, the second face of the dome-shaped septum does not define a recess for receipt of the skirt. In some embodiments, the floating stopper 100 comprises a molded, elastomer material, such as isoprene rubber.

The floating stopper 100 separates the interior of the syringe barrel 82 into a primary fluid chamber 140, defined between itself and the distal end 86 of the barrel; and a secondary fluid chamber 142 defined between itself and the plunger stopper 96. Translation of the plunger 94 generates a differential pressure P on the floating stopper 100, wherein withdrawing the plunger translates the floating stopper towards the proximal end 84 of the syringe barrel 82. Conversely, advancing the plunger 94 translates the floating stopper 100 towards the distal end 86 of the syringe barrel 82. When the central slit 122 of the dome-shaped septum 110 is closed, the secondary fluid chamber 142 is isolated from the outlet lumen 90, so that translation of the plunger 94 only aspirates fluid into or dispenses fluid out of the primary chamber 140, via the outlet lumen 90.

The septum wall 113 of the dome-shaped septum 110 forms a bi-stable valve, conceptually similar to that of the dome-shaped septum 58 of the syringe 20 of FIGS. 1-3. In the embodiment of FIGS. 4-10, the bi-stable valve closes the central slit 124 by compression of the dome-shaped septum 110 in its meridial dimension when the septum is in a first, default, relaxed state, with its the apex 112 closer to the first axial end 104 of the drum-shaped side wall 102. The dome-shaped septum 110 remains in its relaxed, closed, state unless (FIG. 5) and until it is buckled and extended under tension in its meridial dimension (i.e., flipped, shown in FIG. 6) in a second state, with its apex 112 further away from the first axial end 104 of the drum-shaped side wall 102. When the dome-shaped septum 110 is in its second, buckled state, its central slit 122 opens, allowing fluid to flow out of the secondary chamber 142, through the internal stopper cavity 106, out of its second face 116. Thereafter the fluid flows through the primary chamber 140, whereupon it is dispensed or discharged through the outlet lumen 90. Buckling and extension of the dome-shaped septum 110 to its second state also assists folding of the skirt 126 toward the second face 116 and the recess 130.

Buckling or flipping of the wall 113 of the dome-shaped septum 110 is caused solely by application of sufficiently high, buckling differential fluid pressure $P_B$, on the floating stopper 100 by pressing and translating the plunger 94 towards the distal end 86 of the barrel 82. When the plunger 94 is pressed with sufficient force to exceed the buckling differential fluid pressure level $P_B$ within the internal cavity 106 of the floating stopper 100 on the first face 114 of the dome-shaped septum 110, its septum wall 113 buckles to its second state shown in FIG. 6, without physical contact of the septum wall with any other structure within the syringe 80. When differential pressure P on the first face 114 falls below the buckling differential pressure $P_B$, unless otherwise blocked by the barrel protrusion 132 as shown in FIG. 6, the dome-shape stopper 110 relaxes to its first state, closing the central slit 122, thereby re-closing the bi-stable valve and re-isolating the secondary chamber 142 from the first chamber 140. In some embodiments, the buckling differential pressure $P_B$ is greater than approximately 30 pounds per square inch (2.07 bar).

Referring to FIGS. 5 and 6, the distal end 86 of the syringe barrel 82 forms a generally tubular barrel protrusion 132, which is inwardly projecting towards the dome-shaped septum 110 of the floating stopper 100, and coaxially aligned with the axis of the barrel and the central slit 122. The barrel protrusion 132 has a generally frusto-conical tubular profile with a tapered side wall 133 that defines one or more through-notches 134, for fluid communication between the primary chamber 140 and a fluid passage 136 within the barrel protrusion. The fluid passage 136 formed in the barrel protrusion 132 facilitates fluid communication between the primary chamber 140 and the outlet lumen 90, through the one or more through-notches 134 about the circumference of the side wall 133 and axially through the blunt tip 138. In other embodiments, the tubular barrel protrusion 132 defines other profiles.

FIGS. 4, 5, and 6 show interaction of the some-shaped septum 110, the skirt 126 and the barrel protrusion 132 of the syringe 80, where the secondary fluid chamber 142 contains fluid, while the primary fluid chamber 140 at most contains residual fluid between the floating stopper 100 and the distal end 86 of the syringe barrel 82. In FIG. 5, the dome-shaped septum 110 is in its first relaxed state, with its central slit 122 closed. The second axial face 128 of the skirt 126 is axially projecting toward and abutting the distal end 86 of the syringe barrel 82. In this position, the skirt 126 prevents entry of the barrel protrusion 132 into the central slit 132 of the septum 110. Any fluid in the primary fluid chamber 140 is in communication with the through-notch 134 and can flow through the fluid passage 136 of the barrel protrusion 132 and out the outlet lumen 90 of the syringe 80. Conversely, any fluid in the secondary fluid chamber 142 cannot pass through the closed central slit 122 and is isolated from the outlet lumen 90. As the dome-shaped septum 110 is in its first, relaxed state, with the central slit 122 closed, pressure in the secondary fluid chamber 142 is below the buckling pressure necessary to buckle or flip the septum to its second state. Referring to FIGS. 4 and 6, when the plunger 94 is advanced with sufficient force to raise pressure in the secondary fluid chamber 142 above the buckling pressure $P_B$ of the floating stopper 100, the dome-shaped septum 110 buckles or flips to its second state, opening the central slit 122 and rotating/folding the skirt 126 about the latter's skirt hinge 124. As the plunger 94 is further advanced, the barrel protrusion 132 enters the now opened central slit 122, thereby allowing fluid in the secondary fluid chamber 142 to flow through the fluid passage 136 and the outlet lumen 90. Further advancement of the plunger 94 discharges fluid out of the secondary chamber 142 through the outlet lumen. Entry of the barrel protrusion 132 into the central slit 122, effectively blocks the dome-shaped septum from relaxing fully back to its initial state. Rather, the septum wall 113 pliably conforms to abutting contact with the tapered side wall 133 of the barrel protrusion 132. Therefore, subsequent reduction of the advancement force and pressure applied to the plunger 94 can be reduced below the buckling pressure $P_B$ while still discharging fluid from the secondary chamber 142.

In one or more embodiments, the primary chamber 140 is pre-filled or filled on site with a desired medicine. In one or more embodiments, the secondary chamber 142 is pre-filled with a desired amount of a saline flush fluid. In one or more embodiments, the secondary chamber 142 is filled with a desired medicine. In one or more embodiments, both the primary 140 and secondary 142 chambers are filled with a desired medicine. In one or more embodiments, both the primary 140 and secondary 142 chambers are filled with desired amounts of saline flush fluid. In one or more embodiments, the primary chamber 140 and/or the secondary chamber 142 are pre-filled with fluid during or after the assembly of the syringe 80 using sterile filling methods. In some embodiments, the connector 88 and its outlet lumen 90 are capped (not shown) to prevent fluid leakage from the syringe 80. In some applications, the syringe 80 with a capped connector 88 is utilized to reconstitute a powdered medicine that has been prefilled in the primary chamber 140, by dispersing pre-filled diluent liquid stored in the secondary chamber 142 into the primary chamber prior to uncapping the connector.

In other applications, such as shown in FIGS. 4-10, a drug is aspirated and dispensed into a VAD with the primary chamber 140 and subsequently the VAD is flushed with a flushing solution that was pre-filled in the secondary chamber 142 during syringe 80 assembly. A removable, c-shaped collar 144 is applied about the exposed portion of the plunger 94 to inhibit its inadvertent advancement and unintentional discharge of the flushing solution out of the syringe 80. The collar 144 is removed by an administering health care professional prior to syringe use.

Figure 7:
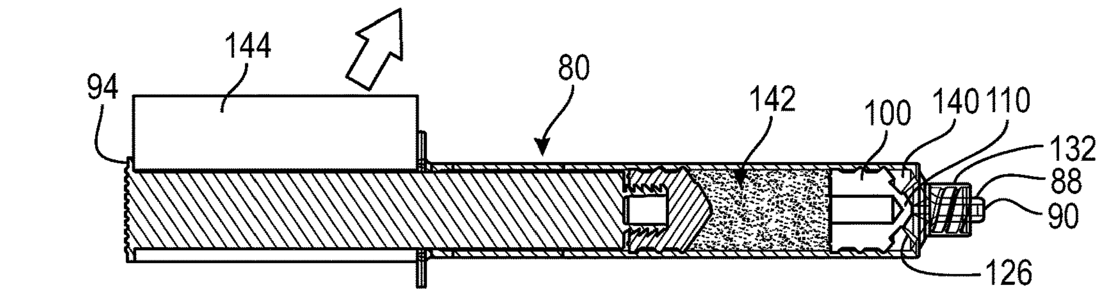
FIGS. 7-10 are illustrative, sequential steps, respectively showing aspiration and dispensing/infusing of a fluid in the primary chamber, such as a drug, followed by dispensing fluid from the secondary chamber.
Figure 8:
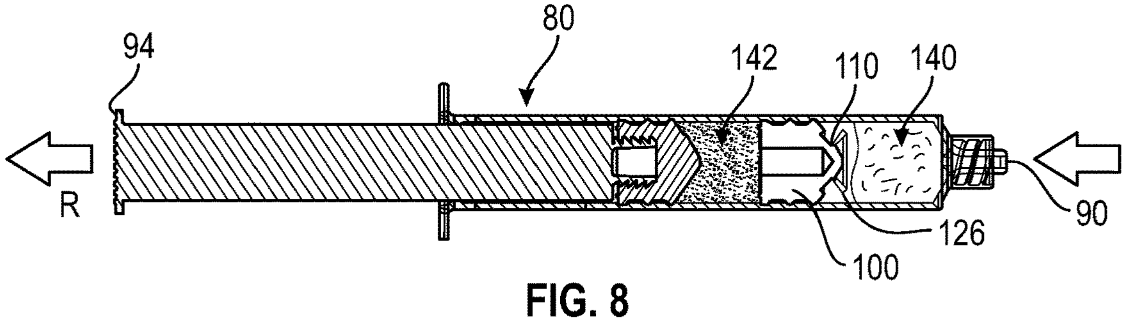
Figure 9:
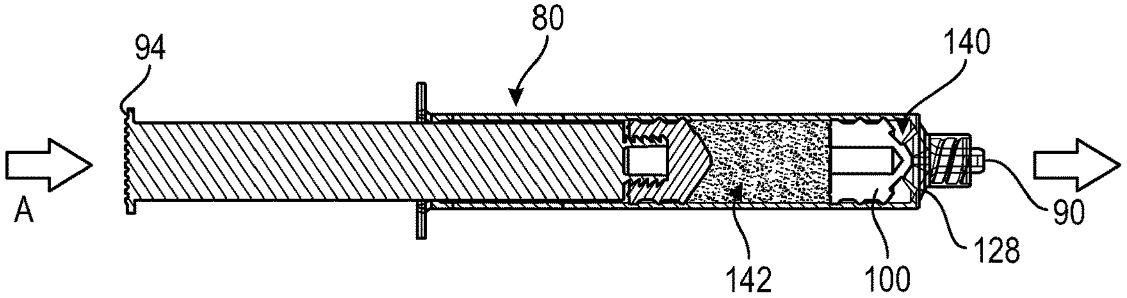
Figure 10:
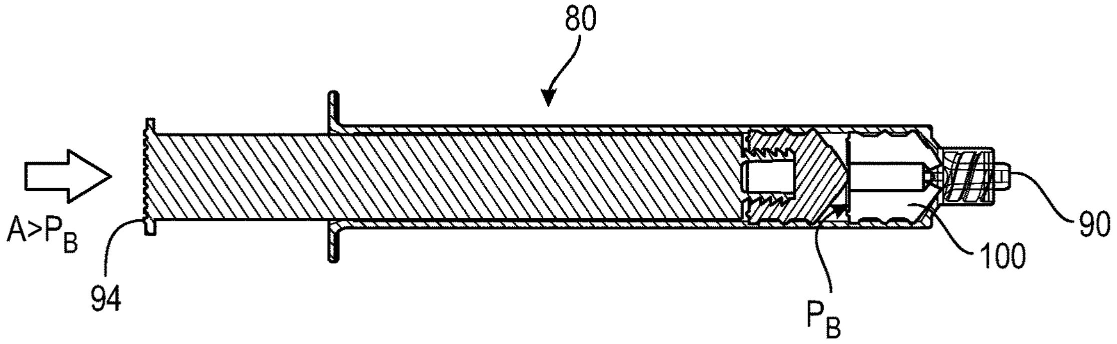

FIGS. 7-10 depict functional operation of the syringe 80, wherein the secondary fluid chamber 142 is prefilled with fluid, such as a flushing fluid, while the primary chamber 140 is empty. In FIG. 7, the administering health care professional removes the collar 144, thereby allowing manipulation of the plunger 94 through its full range of motion. The extended skirt 126 of the floating stopper 100 blocks insertion of the barrel protrusion 132 into the dome-shaped septum 110. While not shown in the figure, the health care professional affixes a needle to the Luer connector 88 for aspiration of a desired medication from a drug vial or other vessel into the empty primary chamber 140 of the syringe 80. In FIG. 8, the plunger 94 is retracted in the direction of the arrow R, which aspirates medication into the primary fluid chamber 140 from the vial. The medication is infused from the primary chamber 140 into a previously flushed VAD of a patient, by advancing the plunger 94 in the direction of the arrow A, with sufficient pressure force below the buckling pressure of the dome-shaped septum 110 to empty the primary chamber, while maintaining the septum in its first, relaxed state (FIG. 5). After medication administration to the patient, the VAD is flushed with flushing solution (e.g., saline or heparin) pre-packaged in the secondary chamber 142 by advancing the plunger rod 94 with sufficient force A to exceed the buckling pressure $P_B$, of the dome-shaped septum 110. Upon completion of the flushing procedure, syringe 80 is then withdrawn from the VAD.

The syringe embodiments disclosed herein are constructed from medical grade materials known to one skilled in the art. In some embodiments, described barrels, plungers and shafts are fabricated with polypropylene polymers.

Seals are fabricated with fiber-filled polytetrafluoroethylene (PTFE) polymers. Stoppers are fabricated with polyisoprene polymers.

Reference throughout this specification to "one embodiment," "certain embodiments," "various embodiments," "one or more embodiments" or "an embodiment" means that a particular feature, structure, material, or characteristic described in connection with the embodiment is included in at least one embodiment of the disclosure. Thus, the appearances of the phrases such as "in one or more embodiments," "in certain embodiments," "in various embodiments," "in one embodiment" or "in an embodiment" in various places throughout this specification are not necessarily referring to the same embodiment of the disclosure. Furthermore, the particular features, structures, materials, or characteristics may be combined in any suitable manner in one or more embodiments. In addition, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are to be interpreted broadly; they encompass direct and indirect mountings, connections, supports, and couplings. Further, "connected" and "coupled" are not restricted to physical, mechanical, or electrical connections or couplings.

Although the disclosure herein provided a description with reference to embodiments, it is to be understood that these embodiments are merely illustrative of the principles and applications of the disclosure. It will be apparent to those skilled in the art that various modifications and variations can be made to the present disclosure without departing from the spirit and scope thereof. Thus, it is intended that the present disclosure include modifications and variations that are within the scope of the appended claims and their equivalents. The appended claims are not limited to the exemplary embodiment details of construction and the arrangement of components set forth in the description or illustrated in the drawings.

What is claimed is:

1. A syringe comprising:

a substantially cylindrically shaped barrel, which defines a first inner side wall, the barrel having an open proximal end, and a distal end, the distal end of the barrel including a connector defining an outlet lumen therethrough, the outlet lumen in fluid communication with an interior of the barrel, the interior defined by the open proximal end, the distal end, and the first inner side wall of the barrel;

a plunger having proximal and distal ends, the distal end thereof disposed within the barrel interior, capable of selective translation within the barrel interior along an axis thereof;

a plunger stopper, coupled to the distal end of the plunger, the plunger stopper having a distal end surface facing the distal end of the barrel;

a monolithic, unistructural, floating stopper oriented in the barrel interior and translatable between the plunger stopper and the distal end of the barrel, the floating stopper having a drum-shaped side wall defining a stopper internal cavity in open communication with a first axial end thereof, a second axial end of the drum-shaped side wall cojoined with a circumferential base of a dome-shaped septum defining an apex, a wall forming the septum having a first face in communication with the stopper internal cavity, and a second face, the septum wall further defining a central slit piercing both its first and second faces at the apex, the septum wall of the dome-shaped septum forming a bi-stable valve, closing the central slit by compression in its meridial dimension when the septum is in a first, relaxed state, and opening the central slit when the septum is buckled under tension in the meridial dimension in a second state, the opened central slit allowing pressurized fluid to flow from the internal stopper cavity out of the second face of the septum, with buckling of the septum wall caused solely by higher differential fluid pressure in the stopper internal cavity on the first face than on its second face, without physical contact of the septum wall with any other structure within the syringe;

a primary fluid chamber, within the barrel interior, defined between the septum of the floating stopper and the outlet lumen, the primary fluid chamber in fluid communication with the central slit of the septum, volume of the primary fluid chamber being selectively variable by translation of the plunger; and a secondary fluid chamber within the barrel interior, defined between the distal end surface of the plunger stopper and the septum of the floating stopper, the secondary fluid chamber in fluid communication with the central slit of the septum, volume and fluid pressure within the secondary fluid chamber being selectively variable by translation of the plunger;

wherein, when the central slit of the septum is closed the secondary fluid chamber is isolated from the outlet lumen, so that translation of the plunger only aspirates fluid into or dispenses fluid out of the primary chamber, via the outlet lumen; and wherein, when the central slit of the septum is opened by increasing differential fluid pressure in the secondary fluid chamber and in the stopper internal cavity, sufficient to buckle the wall of the dome-shaped septum into its second state, the secondary fluid chamber is in fluid communication with the outlet lumen, so that further translation of the plunger toward the distal end of the barrel dispenses fluid out of the secondary chamber, via the outlet lumen.

2. The syringe of claim 1, further comprising the first face of the septum wall defining a notch outwardly diverging from the central slit towards the first axial end of the floating stopper.

3. The syringe of claim 1, wherein the dome-shaped septum buckles from its first relaxed state to its second state upon application of differential fluid pressure in the stopper internal cavity greater than approximately 30 pounds per square inch (2.07 bar).

4. The syringe of claim 1, the floating stopper further comprising a skirt having a first axial face concentrically joined to the second face of the septum wall by an annular skirt hinge that circumscribes the central slit thereof, and a second axial face, projecting from the skirt hinge, in opposed orientation with the distal end of the barrel, whereupon buckling of the septum wall to its second state folds or pivots the skirt about the annular skirt hinge toward the second face of the septum wall.

5. The syringe of claim 4, further comprising the barrel distal end forming a protrusion inwardly projecting towards the dome-shaped septum of the floating stopper, coaxial with the barrel axis, which is received within the central slit when the septum wall is in its second state.

6. The syringe of claim 5, the protrusion further comprising a blunt-tipped tube in fluid communication with the outlet lumen of the connector.

7. The syringe of claim 1, further comprising the barrel distal end forming a protrusion inwardly projecting towards the dome-shaped septum of the floating stopper, coaxial with the barrel axis, which is received within the central slit when the septum wall is in its second state.

8. The syringe of claim 1, further comprising the first face of the septum wall defining the apex of the dome-shaped septum.

9. The syringe of claim 1, further comprising the second face of the septum wall defining the apex of the dome-shaped septum.

10. A syringe comprising:

a substantially cylindrically shaped barrel, which defines a first inner side wall, the barrel having an open proximal end, and a distal end, the distal end of the barrel including a connector defining an outlet lumen therethrough, the outlet lumen in fluid communication with an interior of the barrel, the interior defined by the open proximal end, the distal end, and the first inner side wall of the barrel;

a plunger having proximal and distal ends, the distal end thereof disposed within the barrel interior, capable of selective translation within the barrel interior along an axis thereof;

a plunger stopper, coupled to the distal end of the plunger, the plunger stopper having a distal end surface facing the distal end of the barrel;

a monolithic, unistructural, floating stopper oriented in the barrel interior and translatable between the plunger stopper and the distal end of the barrel, the floating stopper having a drum-shaped side wall defining a stopper internal cavity in open communication with a first axial end thereof, a second axial end of the drum-shaped side wall cojoined, by an intermediary, annular-shaped, flexible hinge, with a circumferential base of a dome-shaped septum defining an apex, a wall forming the septum having a first face in communication with the stopper internal cavity, and a second face, the septum wall defining a central slit piercing both its first and second faces at the apex;

the septum wall of the dome-shaped septum forming a bi-stable valve, closing the central slit by compression in its meridial dimension when the septum is in a first, relaxed state, with the apex is closer to the first axial end of the drum-shaped side wall, and opening the central slit when the septum is buckled under tension in the meridial dimension in a second state, with the apex further away from the first axial end of the drum-shaped side wall, the opened central slit allowing pressurized fluid to flow from the internal stopper cavity out of the second face of the septum, with buckling of the septum wall caused solely by higher differential fluid pressure in the stopper internal cavity on the first face than on its second face, without physical contact of the septum wall with any other structure within the syringe;

a primary fluid chamber, within the barrel interior, defined between the septum of the floating stopper and the outlet lumen, the primary fluid chamber in fluid communication with the central slit of the septum, volume of the primary fluid chamber being selectively variable by translation of the plunger; and a secondary fluid chamber within the barrel interior, defined between the distal end surface of the plunger stopper and the septum of the floating stopper, the secondary fluid chamber in fluid communication with the central slit of the septum, volume and fluid pressure within the secondary fluid chamber being selectively variable by translation of the plunger;

wherein, when the central slit of the septum is closed the secondary fluid chamber is isolated from the outlet lumen, so that translation of the plunger only aspirates fluid into or dispenses fluid out of the primary chamber, via the outlet lumen; and wherein, when the central slit of the septum is opened by increasing differential fluid pressure in the secondary fluid chamber and in the stopper internal cavity, sufficient to buckle the wall of the dome-shaped septum into its second state, the secondary fluid chamber is in fluid communication with the outlet lumen, so that further translation of the plunger toward the distal end of the barrel dispenses fluid out of the secondary chamber, via the outlet lumen.

11. The syringe of claim 10, further comprising the first face of the septum wall defining a notch outwardly diverging from the central slit towards the first axial end of the floating stopper.

12. The syringe of claim 10, wherein the dome-shaped septum buckles from its first relaxed state to its second state upon application of differential fluid pressure in the stopper internal cavity greater than approximately 30 pounds per square inch (2.07 bar).

13. The syringe of claim 10, further comprising the septum wall increasing in thickness from the base to the apex of the dome-shaped septum.

14. The syringe of claim 10, further comprising the first face of the septum wall defining the apex of the dome-shaped septum.

15. A syringe comprising:

a substantially cylindrically shaped barrel, which defines a first inner side wall, the barrel having an open proximal end, and a distal end, the distal end of the barrel including a connector defining an outlet lumen therethrough, the outlet lumen in fluid communication with an interior of the barrel, the interior defined by the open proximal end, the distal end, and the first inner side wall of the barrel;

a plunger having proximal and distal ends, the distal end thereof disposed within the barrel interior, capable of selective translation within the barrel interior along a barrel axis thereof;

a plunger stopper, coupled to the distal end of the plunger, the plunger stopper having a distal end surface facing the distal end of the barrel;

a monolithic, unistructural, floating stopper oriented in the barrel interior and translatable between the plunger stopper and the distal end of the barrel, the floating stopper having a drum-shaped side wall defining a stopper internal cavity in open communication with a first axial end thereof, a second axial end of the drum-shaped side wall cojoined with a circumferential base of a dome-shaped septum defining an apex, a wall forming the septum having a first face in communication with the stopper internal cavity, and a second face in opposed orientation with the distal end of the barrel, the septum wall defining a central slit piercing both its first and second faces at the apex, the floating stopper further defining a skirt having a first axial face concentrically joined to the second face of the septum wall by an annular skirt hinge that circumscribes the central slit thereof, and a second axial face, projecting from the skirt hinge, in opposed orientation with the distal end of the barrel, the septum wall of the dome-shaped septum forming a bi-stable valve, closing the central slit by compression in its meridial dimension when the septum is in a first, relaxed state, with the apex closer to the first axial end of the drum-shaped side wall, and opening the central slit when the septum is buckled under tension in the meridial dimension in a second state, with the apex farther away from the first axial end of the drum-shaped side wall, the opened central slit allowing pressurized fluid to flow from the internal stopper cavity out of the second face of the septum, with buckling of the septum wall caused solely by higher differential fluid pressure in the stopper internal cavity on the first face than on its second face, without physical contact of the septum wall with any other structure within the syringe;

a primary fluid chamber, within the barrel interior, defined between the septum of the floating stopper and the outlet lumen, the primary fluid chamber in fluid communication with the central slit of the septum, volume of the primary fluid chamber being selectively variable by translation of the plunger; and a secondary fluid chamber within the barrel interior, defined between the distal end surface of the plunger stopper and the septum of the floating stopper, the secondary fluid chamber in fluid communication with the central slit of the septum, volume and fluid pressure within the secondary fluid chamber being selectively variable by translation of the plunger;

wherein, when the central slit of the septum is closed the secondary fluid chamber is isolated from the outlet lumen, so that translation of the plunger only aspirates fluid into or dispenses fluid out of the primary chamber, via the outlet lumen; and wherein, when the central slit of the septum is opened by increasing differential fluid pressure in the secondary fluid chamber and in the stopper internal cavity, sufficient to buckle the wall of the dome-shaped septum into its second state, the skirt folds or pivots about the annular skirt hinge toward the second face of the septum wall, and the secondary fluid chamber is in fluid communication with the outlet lumen, so that further translation of the plunger toward the distal end of the barrel dispenses fluid out of the secondary chamber, via the outlet lumen.

16. The syringe of claim 15, wherein the dome-shaped septum buckles from its first relaxed state to its second state upon application of differential fluid pressure in the stopper internal cavity greater than approximately 30 pounds per square inch (2.07 bar).

17. The syringe of claim 15, the skirt of the floating stopper further comprising a frusto-conical-shaped skirt having a narrower diameter, first axial face concentrically joined to the second face of the septum wall by the annular skirt hinge that circumscribes the central slit thereof, and a diverging second axial face, projecting from the skirt hinge, in opposed orientation with the distal end of the barrel, whereupon buckling of the septum wall to its second state folds or pivots the skirt about the annular skirt hinge toward the second face of the septum wall.

18. The syringe of claim 17, further comprising the second face of the septum wall defining a recess for receipt of the folding or pivoting skirt when the septum wall buckles to its second state.

19. The syringe of claim 18, wherein the skirt blocks contact between the central slit and the distal end of the barrel when the septum wall is in its first state.

20. The syringe of claim 18, further comprising the barrel distal end forming a protrusion inwardly projecting towards the dome-shaped septum of the floating stopper, coaxial with the barrel axis, which is received within the central slit when the septum wall is in its second state.

21. The syringe of claim 20, the protrusion further comprising a blunt-tipped tube in fluid communication with the outlet lumen of the connector.

22. The syringe of claim 15, further comprising the second face of the septum wall defining a recess for receipt of the folding or pivoting skirt when the septum wall buckles to its second state.

23. The syringe of claim 15, wherein the skirt blocks contact between the central slit and the distal end of the barrel when the septum wall is in its first state.

24. The syringe of claim 15, further comprising the barrel distal end forming a protrusion inwardly projecting towards the dome-shaped septum of the floating stopper, coaxial with the barrel axis, which is received within the central slit when the septum wall is in its second state.

25. The syringe of claim 24, the protrusion further comprising a blunt-tipped tube in fluid communication with the outlet lumen of the connector.

26. The syringe of claim 24, further comprising a circumferential surface of the tube defining through-apertures for establishing fluid communication between an interior of the tube and the outlet lumen of the connector.

27. The syringe of claim 15, further comprising the second face of the septum wall defining the apex of the dome-shaped septum.

* * * * *